United States Patent [19]

Yano et al.

[11] Patent Number: 4,689,340
[45] Date of Patent: Aug. 25, 1987

[54] TRIHALOIMIDAZOLE INSECTICIDE

[75] Inventors: Toshihiko Yano, Ikoma; Yoji Takada; Hiroki Tomioka, both of Takarazuka; Naonori Hirata, Sakai, all of Japan

[73] Assignee: Sumitomo Chemical Company, Limited, Osaka, Japan

[21] Appl. No.: 797,943

[22] Filed: Nov. 14, 1985

[30] Foreign Application Priority Data

Aug. 15, 1985 [JP] Japan ................................. 60-179790

[51] Int. Cl.⁴ .................... C07D 233/66; A01N 43/50
[52] U.S. Cl. ..................................... 514/399; 548/337
[58] Field of Search ........................ 548/337; 514/399

[56] References Cited

U.S. PATENT DOCUMENTS 3,435,050 3/1969 Wasco ................................. 548/337
3,674,874 7/1972 Rutz et al. ........................... 548/337
3,759,945 9/1973 Rutz et al. ........................... 548/337

FOREIGN PATENT DOCUMENTS 485733 3/1970 Switzerland ....................... 548/337
1197102 7/1970 United Kingdom ............... 548/337
1316665 5/1973 United Kingdom ............... 548/337

Primary Examiner—John M. Ford
Assistant Examiner—Robert C. Whittenbaugh
Attorney, Agent, or Firm—Stevens, Davis, Miller & Mosher

[57] ABSTRACT

The present invention relates to a trihaloimidazole derivative represented by the formula,

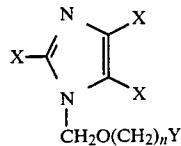

wherein X and Y, being the same or different, each represent a halogen atom, and n represents an integer of 4 to 6, its production and an insecticidal composition containing it as an active ingredient.

29 Claims, No Drawings

TRIHALOIMIDAZOLE INSECTICIDE

The present invention relates to a trihaloimidazole derivative represented by the formula (I) (hereinafter referred to as present compound),

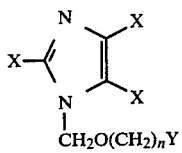

(I)

wherein X and Y, being the same or different, each represent a halogen atom, and n represents an integer of 4 to 6, its production and an insecticidal composition containing it as an active ingredient.

A halogen atom that X and Y represent includes chlorine, bromine, iodine and fluorine atoms.

The present inventors extensively studied to find a compound having a more superior insecticidal activity, and as a result, found that the present compound represented by the formula (I) has excellent properties as follows:

1. Insecticidal activity is very high.
2. Effect on cockroaches is particularly high with excellent knocked-down and lethal activities.
3. Insecticidal effect on German cockroaches low susceptible to pyrethroids is remarkable.
4. Effect as fumigants is high.
5. Toxicity to mammals is relatively low.

It is described in B.P. No. 1,316,665, U.S Pat. Ser. No. 3,674,874, etc. that a certain kind of trihaloimidazole derivative, for example 1-n-pentyloxymethyl-2,4,5-trichloroimidazole, 1-isopropoxymethyl-2,4,5-trichloroimidazole, 1-(2-bromoethyl)oxymethyl-2,4,5-tribromoimidazole, etc., can be used as an active ingredient for insecticidal and/or acaricidal composition.

The present compound is included in the scope of the formula described in U.S. Pat. No. 3,674,874, but it is not concretely referred to at all in said patent. But, the present inventors, as clearly shown in the test examples described later, found that the present compound has an extremely high insecticidal activity as compared with the homologues described in said patent, and besides that it has entirely new insecticidal characteristics in terms of an insecticidal effect on German cockroaches low susceptible to pyrethroids and an effect as fumigant. The present inventors thus attained to the present invention.

The present compound, therefore, can be used as an active ingredient for insecticidal compositions which displays an effect on insect pests in question in many scenes. Particularly, it is expected to be used as the active ingredient of fumigants for controlling cockroaches such as German cockroach (*Blattella germanica*), American cockroach (*Periplaneta americana*), smoky brown cockroach (*Periplaneta fuliginosa*), etc Among the present compounds, those having a high insecticidal activity particularly as cockroach-controlling insecticides include the followings:

1-(4-bromobutoxymethyl)-2,4,5-trichloroimidazole,
1-(4-chlorobutoxymethyl)-2,4,5-trichloroimidazole,
1-(4-bromobutoxymethyl)-2,4,5-tribromoimidazole,
1-(4-chlorobutoxymethyl)-2,4,5-tribromoimidazole,
1-(6-bromohexyloxymethyl)-2,4,5-trichloroimidazole,
1-(6-bromohexyloxymethyl)-2,4,5-tribromoimidazole, etc.

of these compounds, 1-(4-bromobutoxymethyl)-2,4,5-trichloroimidazole displays the most superior insecticidal activity.

The present compounds can be produced by reacting a trihaloimidazole represented by the formula (II),

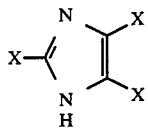

(II)

wherein X represents a halogen atom, with a halomethyl ether represented by the formula (III),

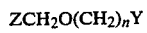

ZCH$_2$O(CH$_2$)$_n$Y  (III)

wherein Y and Z, being the same or different, each represent a halogen atom, and n represents an integer of 4 to 6, at about 0° C. to about 150° C. for about 1 to about 24 hours in a solvent in the presence of a dehydrohalogenating agent.

Hereupon, a halogen atom that Z represents includes a chlorine and bromine atoms, etc.

The solvent used in this reaction includes for example aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, ethylene glycol dimethyl ether), ketones (e.g. acetone, methyl ethyl ketone, methyl isobutyl ketone, isophorone, cyclohexanone), esters (e.g. ethyl formate, ethyl acetate, butyl acetate, diethyl carbonate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. formamide, N,N-dimethylformamide, N,N-dimethylacetamide), sulfur compounds (e.g. dimethyl sulfoxide, sulfolane) and mixtures thereof.

The dehydrohalogenating agent includes for example organic bases (e.g. pyridine, triethylamine, N,N-diethylaniline), inorganic bases (e.g. sodium hydroxide, potassium hydroxide, sodium carbonate, potassium carbonate, sodium hydride), alkali metal alkoxides (e.g. sodium methoxide, sodium ethoxide) and the like.

After completion of the reaction, the usual after-treatment is applied, and if necessary, purification by chromatography, distillation, etc. may be applied.

Of the starting materials for the present compounds, 2,4,5-tribromoimidazole can be produced by bromination of imidazole, and 2,4,5-trichloroimidazole can be produced, for example, by a method described in U.S. Pat. No. 3,435,050 and Swiss Patent No. 485,733.

PRODUCTION EXAMPLE 1 [PRODUCTION OF THE PRESENT COMPOUND (1)]

To a mixture of 1.03 g of 2,4,5-trichloroimidazole, 0.61 g of triethylamine and about 30 ml of toluene was added dropwise 1.48 g of 4-bromobutoxymethyl bromide at room temperature. After stirring this mixture at room temperature for 2 hours, the deposited crystal was filtered off and washed with about 10 ml of toluene.

The filtrate thus obtained was concentrated under reduced pressure, and the residual oily product was purified by column chromatography on silica gel to obtain 0.78 g of 1-(4-bromobutoxymethyl)-2,4,5-trichloroimidazole.

$n_D^{23.7} 1.5337$

PRODUCTION EXAMPLE 2 [PRODUCTION OF THE PRESENT COMPOUND (2)]

To a solution of a sodium salt, prepared from 0.69 g of 2,4,5-trichloroimidazole and 0.16 g of 60% oil-based sodium hydride, in 5 ml of N,N-dimethylformamide was added dropwise 0.63 g of 4-chlorobutoxymethyl chloride at room temperature. After stirring at room temperature for 3 hours, 50 ml of water was added to the reaction mixture which was then extracted with three 30-ml portions of ether. The ether layer was dried over magnesium sulfate and concentrated. The oily product obtained was purified by column chromatography on silica gel to obtain 0.83 g of 1-(4-chlorobutoxymethyl)-2,4,5-trichloroimidazole.

$n_D^{26.8} 1.5140$

PRODUCTION EXAMPLE 3 [PRODUCTION OF THE PRESENT COMPOUND (3)]

To a solution of a sodium salt, prepared from 1.22 g of 2,4,5-tribromoimidazole and 0.16 g of 60% oil-based sodium hydride, in 5 ml of N,N-dimethylformamide was added dropwise 1.23 g of 4-bromobutoxymethyl bromide at room temperature. After stirring at room temperature for 3 hours, 50 ml of water was added to the reaction mixture which was then extracted with three 30-ml portions of ether. The ether layer was dried over magnesium sulfate and concentrated. The oily product obtained was purified by column chromatography on silica gel to obtain 0.74 g of 1-(4-bromobutoxymethyl)-2,4,5-tribromoimidazole.

$n_D^{21.7} 1.5797$

Some of the present compounds which can be produced by the method described above will be shown in Table 1.

TABLE 1

Trihaloimidazole derivatives represented by the formula,

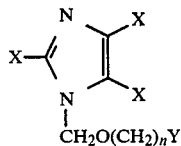

| Compound No. | Structural formula | | | Physical constant |
|---|---|---|---|---|
| | n | X | Y | |
| (1) | 4 | Cl | Br | $n_D^{23.7}$ 1.5337 |
| (2) | 4 | Cl | Cl | $n_D^{26.8}$ 1.5140 |
| (3) | 4 | Br | Br | $n_D^{21.7}$ 1.5797 |
| (4) | 4 | Br | Cl | $n_D^{27.8}$ 1.5620 |
| (5) | 5 | Cl | Br | $n_D^{24.0}$ 1.5289 |
| (6) | 6 | Cl | Br | $n_D^{25.8}$ 1.5248 |
| (7) | 6 | Br | Br | $n_D^{27.0}$ 1.5667 |

When the present compounds are used as an active ingredient for insecticidal compositions, they may be used as such without adding any other ingredients. Generally, however, they are formulated into emulsifiable concentrates, wettable powders, dusts, granules, oil sprays, aerosols, heating fumigants (e.g. mosquito coils, electric mosquito mats, porous ceramic plates, "rod" type formulations, "jet" type formulations, foggings, non-heating fumigants, poisonous baits, etc. by mixing with solid carriers, liquid carriers, gaseous carriers, surface active agents, other auxiliaries for formulation, baits, etc., or impregnating into bases such as mosquito coil carriers, mats, etc.

As described above, the insecticidal composition of the present invention is particularly suitable for the control of cockroaches so that, in using it for such purpose, its insecticidal effect can be developed more efficiently by using it in the form of a fumigant. The fumigant means one of the pesticide formulations which controls pests or fungi by dispersing the active ingredients into atmosphere in some way.

As the form of such fumigant, there may be given, for example, types suitable for non-heating (e.g. mothprofer strip, insecticidal strip, mothball), burning (e.g. "jet" type formulations, "rod" type formulations, mosquito coil), exothermic reaction (e.g. types generating heat by water addition or air oxidation), electric heating (e.g. mat) and the like.

As the mothprofer strip or insecticidal strip, there may be given, for example, strips produced by impregnating the paper, pulp, synthetic resin, etc. with an active ingredient.

As the mothball, there may be given, for example, balls produced by hardening an active ingredient as such.

As a main base for the "jet" type formulations, there are given, for example, mixtures of a nitrate or nitrite and a thermal decomposition-stimulating agent (e.g. salts of an alkaline earth metal or alkali metal), mixtures of a guanidine salt and a thermal decomposition-stimulating agent (e.g. bichromates, chromates), and the like.

As a main base for the "rod" type formulations, there are given, for example, mixtures of a burning agent (e.g. ethyl cellulose, nitrocellulose), a flameextinguishing agent (e.g. melamine, flour), a filler (e.g. diatomaceous earth) and a vehicle and the like. This mixture is kneaded and then formed into a rod.

As a main base for mosquito coil, there are given, for example, mixture of a burning agent (e.g. wood powder, pyrethrum marc) and a setting agent (e.g. Tabu powder). This mixture is kneaded and then formed into a mosquito coil.

As a main base for the type which generates heat by air oxidation, there are given, for example, mixtures of a heat-generating agent (e.g. sulfides, polysulfides or hydrosulfides of an alkali metal, their hydrated salts), a catalytic substance (e.g. carbon black, activated carbon, charcoal, coke, asphalt) and a filler (e.g. natural fibers, synthetic fibers, synthetic resin foams), and the like As a main base for the type which generates heat by water addition, there are given, for example, mixtures of an organic foaming agent (e.g. azodicarbonamide, benzenesulfonyl hydrazide) and a heat-generating agent (e.g. calcium oxide), and the like.

As the mat, there may be given, for example, mats produced by impregnating the porous plate of asbestos, pulp, ceramics, etc. with an active ingredient dissolved in an organic solvent such as acetone.

The foregoing compositions contain 0.001 to 95% by weight of the present compound as an active ingredient.

The solid carrier includes for example fine powders or granules of kaoline clay, attapulgite clay, bentonite, terra abla, pyrophyllite, talc, diatomaceous earth, calcite, corn stalk powder, walnut shell powder, urea, ammonium sulfate, synthetic hydrated silicon dioxide and the like. The liquid carrier includes for example aliphatic hydrocarbons (e.g. kerosene), aromatic hydrocarbons (e.g. benzene, toluene, xylene, methylnaphthalene), halogenated hydrocarbons (e.g. dichloroethane, trichloroethylene, carbon tetrachloride), alcohols (e.g. methyl alcohol, ethyl alcohol, isopropyl alcohol, ethylene glycol, cellosolve), ketones (e.g. acetone, methyl ethyl ketone, cyclohexanone, isophorone), ethers (e.g. diethyl ether, dioxane, tetrahydrofuran), esters (e.g. ethyl acetate), nitriles (e.g. acetonitrile, isobutyronitrile), acid amides (e.g. dimethylformamide, dimethylacetamide), dimethyl sulfoxide, vegetable oils (e.g. soybean oil, cotton seed oil) and the like. The gaseous carrier includes for example freon gas, LPG (liquefied petroleum gas), dimethyl ether and the like. The surface active agent used for emulsification, dispersion, wetting, etc. includes for example anionic surface active agents such as the salt of alkyl sulfates, alkyl(aryl)sulfonates, dialkyl sulfosuccinates, the salt of polyoxyethylene alkylaryl ether phosphoric acid ester, naphthalenesulfonic acid/formalin condensates, etc., and nonionic surface active agents such as polyoxyethylene alkyl ether, polyoxyethylene polyoxypropylene block copolymers, sorbitan fatty acid esters, polyoxyethylene sorbitan fatty acid esters, etc. The auxiliary for formulation such as fixing agents, dispersing agents, etc. includes for example lignosulfonates, alginates, polyvinyl alcohol, gum arabic, molasses, casein, gelatin, CMC (carboxymethyl cellulose), pine oil, agar, etc. The stabilizer includes for example alkyl phosphates [e.g. PAP (isopropyl acid phosphate), TCP (tricresyl phosphate)], vegetable oils, epoxidized oils, the foregoing surface active agents, antioxidants (e.g. BHT, BHA), fatty acid salts (e.g. sodium oleate, calcium stearate), fatty acid esters (e.g. methyl oleate, methyl stearate) and the like.

Formulation examples will be shown. The present compounds are shown by Compound No. described in Table 1. Parts in the examples are by weight.

FORMULATION EXAMPLE 1

0.2 Part of the present compound (1), 2 parts of xylene and 97.8 parts of kerosene are mixed to obtain an oil spray.

FORMULATION EXAMPLE 2

Ten parts of each of the present compounds (1) to (7), 14 parts of polyoxyethylene styrylphenyl ether, 6 parts of calcium dodecylbenzenesulfonate and 70 parts of xylene are well mixed to obtain the emulsifiable concentrate of each compound.

FORMULATION EXAMPLE 3

Twenty parts of the present compound (2), 10 parts of fenitrothion, 3 parts of calcium lignosulfonate, 2 parts of sodium lauryl sulfate and 65 parts of synthetic hydrated silicon dioxide are well pulverized and mixed together to obtain a wettable power.

FORMULATION EXAMPLE 4

One part of the present compound (1), 2 parts of Carbaryl, 87 parts of kaoline clay and 10 parts of talc are well pulverized and mixed together to obtain a dust.

FORMULATION EXAMPLE 5

Five parts of the present compound (1), 1 part of synthetic hydrated silicon dioxide, 2 parts of calcium lignosulfonate, 30 parts of bentonite and 62 parts of kaolin clay are well pulverized and mixed together, well kneaded with water, granulated and then dried to obtain a granule.

FORMULATION EXAMPLE 6

0.05 Part of the present compound (1), 0.2 part of tetramethrin, 0.05 part of resmethrin, 7 parts of xylene and 32.7 parts of deodorized kerosene are well mixed into a solution. The solution is filled in an aerosol container, and after attaching a valve portion to the container, 60 parts of a propellant (liquefied petroleum gas) is charged therein through the valve under pressure to obtain an aerosol.

FORMULATION EXAMPLE 7

0.3 Gram of the present compound (1) and 0.3 g of the d-trans-chrysanthemate of allethrin are dissolved in 20 ml of methanol. This solution and 99.4 g of a mosquito coil carrier, which is a 3:5:1 mixture of Tabu powder, Pyrethrum marc and wood powder, are uniformly mixed with stirring. After evaporating methanol, 150 ml of water is added to the residue, and the mixture is well kneaded, shaped and dried to obtain a mosquito coil.

FORMULATION EXAMPLE 8

One hundred mg of each of the present compounds (1) to (7) is dissolved in a proper amount of acetone, and a porous ceramic plate of 4.0 cm×4.0 cm×1.2 cm (thick) is impregnated with this solution to obtain the heating fumigant of each compound.

These compositions are used as such or as aqueous dilute solutions. Also, they may be used in mixture with other insecticides, acaricides, nematocides, fungicides, herbicides, plant growth regulators, fertilizers, soil improvers and the like.

When the present compounds are used in the form of emulsifiable concentrate or wettable powder as an insecticidal composition, their application concentration is 10 to 10000 ppm. When they are used in the form of dust, granule, oil spray or aerosol, they are applied as such without dilution.

Test examples will be shown. Compounds used as a control are shown by Compound symbol in Table 2.

TABLE 2

| Compound symbol | Structural formula | Name |
|---|---|---|
| (A) | Cl—⟨N=Cl / N—Cl⟩ , CH$_2$OC$_4$H$_9$(n) | Compound described in U.S. Pat. No. 3,674,874. |
| (B) | Cl—⟨N=Cl / N—Cl⟩ , CH$_2$OC$_5$H$_{11}$(n) | Compound described in B.P. No. 1,316,665 and U.S. Pat. No. 3,674,874. |
| (C) | Br—⟨N=Br / N—Br⟩ , CH$_2$OCH$_2$CH$_2$Br | Compound described in U.S. Pat. No. 3,674,874. |

TABLE 2-continued

| Compound symbol | Structural formula | Name |
|---|---|---|
| (D) | Br–C(=N–Br)–N(CH$_2$OCH$_2$CH$_2$Cl)–Br | Same as above. |
| (E) | (benzene ring)–O–C(=O)–NHCH$_3$, with OCH(CH$_3$)$_2$ | Propoxur |

TEST EXAMPLE 1

1-1 Acute Oral Toxicity Test to Mice

The present compounds and the control were each diluted with corn oil to prescribed concentrations, and the dilute solutions obtained were forcedly administered to the stomach of six-week old male mice of ICR strain weighing 24 to 31 g, to which no food had been given for about 20 hours, at a rate of 0.1 ml/10 g of body weight. The mice were observed for 4 hours after administration and then bred on bait and water in a cage. The number of the dead and alive was examined by seven day's observation to obtain LD$_{50}$ value ( 50% lethal dosage) (5 mice per group). 1-2 Insecticidal activity test to German cockroach The present compounds and the control were each diluted with acetone to prescribed concentrations and topically applied to the ventral thorax of the male adults of German cockroach (*Blattella germanica*) which belong to a strain low susceptible to pyrethroids, at a rate of 1 μl/adult. After application, the adults were bred on bait and water in a polyethylene cup. After two days, the number of the dead and alive was examined to obtain LD$_{50}$ value (10 adults per group; two replications).

Result:

The results of the acute oral toxicity test to mice and insecticidal activity test to German cockroaches on the test compounds are shown in Table 3. It is apparent from the table that the present compounds have the characteristics that the toxicity to the warm-blooded animal is low and the insecticidal activity on the insect pest is high. In order to make this characteristic clearer, the following safety coefficient was obtained from the test results.

$$\text{Safety coefficient} = \frac{\text{toxicity to mice (LD}_{50}\text{ value mg/kg)}}{\text{insecticidal activity (LD}_{50}\text{ value mg/kg)}}$$

As a result of the calculation, both the present compounds (1) and (2) have a safety coefficient of more than about 50. This means that the present compounds are more than 50 times safer to the warm-blooded animal. On the other hand, the safety coefficients of the controls (C), (D) and (E) were 16, 18 and 5.6, respectively.

TABLE 3

| Test Compound | Acute oral toxicity to mice LD$_{50}$ value (mg/kg) (a) | Insecticidal activity on German cockroaches LD$_{50}$ value (mg/kg) (b) | Safety coefficient (a)/(b) |
|---|---|---|---|
| (1) | >300 | 6.4 | >47 |
| (2) | >300 | 6.2 | >48 |
| (A) | — | >10 | — |
| (B) | — | >20 | — |
| (C) | 110 | 7.0 | 16 |
| (D) | 170 | 9.4 | 18 |
| (E) | 39 | 7.0 | 5.6 |

TEST EXAMPLE 2

The present compounds and the control were each diluted with acetone and topically applied to the ventral thorax of the male adults of smoky brown cockroach (*Periplaneta fuliginosa*) at a rate of 10μg a.i./adult. After application, the adults were bred on bait and water in a polyethylene cup. After two days, the number of the dead and alive was examined to obtain a mortality (5 adults per group; two replications).

The result is shown in Table 4.

TABLE 4

| Test compound | Mortality (%) |
|---|---|
| (1) | 80 |
| (2) | 100 |
| (B) | 40 |
| No treatment | 10 |

TEST EXAMPLE 3

Four polyethylene cups (inside diameter, 10 cm; height, 8 cm) coated with butter at the inside surface were set at the four corners, respectively, of the bottom of a (70 cm)$^3$ glass chamber (0.34 m$^3$). Ten male adults per group of German cockroach (*Blattella germanica*) which belongs to a strain low susceptible to pyrethroids, were liberated in each of two polyethylene cups, and 10 female adults per group of the insect were liberated in each of the remaining two. An electric heater was set at the center of the bottom of the glass chamber, and each of the porous ceramic plates impregnating the present compounds and the control according to Formulation example 8 (13.7 mg/plate: 40 mg/m$^3$), was placed thereon. The plate was heated to about 200° C. by applying current for 20 minutes. The number of knocked-down insects with the lapse of time was examined to obtain KT$_{50}$ (50% knocked-down time). Eighty minutes after current application was started, the cups containing the test insects were taken out of the chamber, and the test insects were bred on water and bait. After two days, the number of the dead and alive was examined to obtain a mortality.

The result is shown in Table 5.

TABLE 5

| Test compound | KT$_{50}$ value (minute) | Mortality (%) |
|---|---|---|
| (1) | 28' | 100 |
| (2) | 41' | 100 |
| (3) | 45' | 100 |
| (4) | 58' | 90 |
| (5) | 68' | 87.5 |
| (7) | 65' | 92.5 |
| (B) | >80' | 47.5 |

TABLE 5-continued

| Test compound | KT$_{50}$ value (minute) | Mortality (%) |
|---|---|---|
| (E) | >80' | 0 |

TEST EXAMPLE 4

At the bottom of a (183 cm)$^3$ Peet Grady's chamber (6.1 m$^3$) were placed three polyethylene cups (inside diameter, 10 cm; height, 8 cm) coated with butter at the inside surface, and 20 adult German cockroaches (10 males and 10 females) (*Blattella germanica*), which belong to a strain low susceptible to pyrethroids were liberated in each cup. An electric heater was set at the center of the bottom of the chamber, and each of the porous ceramic plates impregnated with the present compounds and the control according to Formulation example 8 (61 mg/plate: 10 mg/m$^3$), was placed thereon. The plate was heated to about 200° C. by applying current for 70 minutes. The number of knocked-down insects with the lapse of time was examined to obtain KT$_{50}$ value (50% knocked-down time). Eighty minutes after current application was started, the cups containing the test insects were taken out of the chamber, and the test insects were bred on water and bait. After three days, the number of the dead and alive was examined to obtain a mortality.

The result is shown in Table 6.

TABLE 6

| Test compound | KT$_{50}$ value (minute) | Mortality (%) |
|---|---|---|
| (1) | 38' | 100 |
| (2) | 63' | 80 |
| (3) | 77' | 90 |
| (6) | 41' | 95 |
| (A) | >80' | 8 |
| (B) | >80' | 0 |
| (C) | >80' | 40 |
| (D) | >80' | 3 |
| (E) | >80' | 0 |

TEST EXAMPLE 5

Two groups of five male and five femlae adults per group of German cockroach (*Blattela germanica*), one group belonging to a susceptible strain and the other belonging to a strain low susceptible to pyrethroids, were liberated in a polyethylene cup of 9 cm in diameter thinly coated with vaseline at the inside surface. After covering the cup with a 16-mesh nylon gauze, the cup was placed on the bottom of a glass cylinder (inside diameter, 10 cm; height, 37 cm). Thereafter 0.6 ml of each of the 0.1% oil sprays of the present compounds and the control, prepared according to Formulation example 1, was directly sprayed onto the adults by means of a spray gun under 0.6 atmospheric pressure from the top of the cylinder. The number of knocked-down insects with the lapse of time was counted to obtain KT$_{50}$ value (50% knocked-down time) (two replications).

The result is shown in Table 7.

TABLE 7

| Test compound | Susceptible strain KT$_{50}$ value (minute) | Strain low susceptible to pyrethroids KT$_{50}$ value (minute) |
|---|---|---|
| (1) | 1.1' | 0.70' |
| (3) | 1.1' | 1.2' |
| (4) | 2.1' | ≈0.5' |
| (7) | 2.3' | 0.72' |
| (A) | >20' | >20' |
| (B) | >20' | >20' |
| (C) | >20' | ≧20' |
| (D) | >20 | ≈20 |
| (E) | 6.9' | 10' |

What is claimed is:

1. A trihaloimidazole derivative represented by the formula,

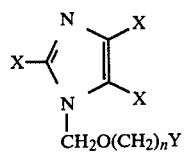

wherein X and Y, being the same or different, each represent a halogen atom, and n represents an integer of 4 to 6.

2. The trihaloimidazole derivative according to claim 1, wherein n represents 4.

3. 1-(4-Bromobutoxymethyl)-2,4,5-trichloroimidazole.

4. 1-(4-Chlorobutoxymethyl)-2,4,5-trichloroimidazole.

5. 1-(4-Bromobutoxymethyl)-2,4,5-tribromoimidazole.

6. 1-(4-Chlorobutoxymethyl)-2,4,5-tribromoimidazole.

7. 1-(6-Bromohexyloxymethyl)-2,4,5-trichloroimidazole.

8. 1-(6Bromohexyloxymethyl)-2,4,5-tribromoimidazole.

9. An insecticidal composition which comprises as an active ingredient an insecticidally effective amount of a trihaloimidazole derivative represented by the formula,

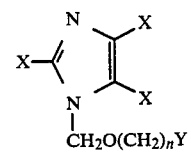

wherein X and Y, being the same or different, each represent a halogen atom, and n represents an integer of 4 to 6, and an inert carrier.

10. The insecticidal composition according to claim 9, wherein the composition is a form of a fumigant for cockroaches.

11. The insecticidal composition according to claim 10, wherein the trihaloimidazole derivative is a trihaloimidazole derivative represented by the formula,

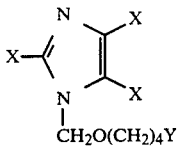

wherein X and Y, being the same or different, each represent a halogen atom.

12. The insecticidal composition according to claim 10, wherein the trihaloimidazole derivative is 1-(4-bromobutoxymethyl)-2,4,5-trichloroimidazole.

13. The insecticidal composition according to claim 10, wherein the trihaloimidazole derivative is 1-(4-chlorobutoxymethyl)-2,4,5-trichloroimidazole.

14. The insecticidal composition according to claim 10, wherein the trihaloimidazole derivative is 1-(4-bromobutoxymethyl)-2,4,5-tribromoimidazole.

15. The insecticial composition according to claim 10, wherein the trihaloimidazole derivative is 1-(4-chlorobutoxymethyl)-2,4,5-tribromoimidazole.

16. The insecticidal composition according to claim 10, wherein the trihaloimidazole derivative is 1-(6-bromohexyloxymethyl)-2,4,5-trichloroimidazole.

17. The insecticidal composition according to claim 10, wherein the trihaloimidazole derivative is 1-(6-bromohexyloxymentyl)-2,4,5-tribromoimidazole.

18. A method for killing insects which comprises applying an insecticidally effective amount of a trihaloimidazole derivative represented by the formula,

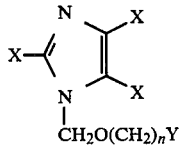

wherein X and Y, being the same or different, each represent a halogen atom, and n represents an integer of 4 to 6, to the insects.

19. The method for killing insects according to claim 18, wherein the insects are cockroaches.

20. The method for killing insects according to claim 19, wherein the trihaloimidazole derivative is a trihaloimidazole derivative represented by the formula,

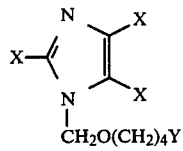

wherein X and Y, being the same or different, each represent a halogen atom.

21. The method for killing insects according to claim 19, wherein the trihaloimidazole derivative is 1-(4-bromobutoxymethyl)-2,4,5-trichloroimidazole.

22. The method for killing insects according to claim 19, wherein the trihaloimidazole derivative is 1-(4-chlorobutoxymethyl)-2,4,5-trichloroimidazole.

23. The method for killing insects according to claim 19, wherein the trihaloimidazole derivative is 1-(4-bromobutoxymethyl)-2,4,5-tribromoimidazole.

24. The method for killing insects according to claim 19, whrein the trihaloimidazole derivative is 1-(4-chlorobutoxymethyl)-2,4,5-tribromoimidazole.

25. The method for killing insects according to claim 19, wherein the trihaloimidazole derivative is 1-(6-bromohexyloxymethyl)-2,4,5-trichloroimidazole.

26. The method for killing insects according to claim 19, wherein the trihaloimidazole derivative is 1-(6-bromohexyloxymethyl)-2,4,5-tribromoimidazole.

27. The trihaloimidazole derivative according to claim 1, wherein X and Y are bromine or chlorine.

28. The insecticidal composition according to claim 9, wherein X and Y are bromine or chlorine.

29. The method according to claim 18, wherein X and Y are bromine or chlorine.

* * * * *